US011581066B2

(12) United States Patent
Liu et al.

(10) Patent No.: US 11,581,066 B2
(45) Date of Patent: Feb. 14, 2023

(54) METHOD OF SIMULTANEOUS MODELING AND COMPLEXITY REDUCTION OF BIO-CRUDES FOR PROCESS SIMULATION

(71) Applicant: Pukyong National University Industry—University Cooperation Foundation, Busan (KR)

(72) Inventors: Jay Liu, Busan (KR); Boris Brigljevic, Susan (KR); Petar Zuvela, Singapore (SG)

(73) Assignee: Pukyong National University—University Cooperation Foundation, Busan (KR)

( * ) Notice: Subject to any disclaimer, the term of this patent is extended or adjusted under 35 U.S.C. 154(b) by 1197 days.

(21) Appl. No.: 16/123,062

(22) Filed: Sep. 6, 2018

(65) Prior Publication Data
US 2019/0362050 A1  Nov. 28, 2019

(30) Foreign Application Priority Data

May 28, 2018  (KR) ........................ 10-2018-0060659

(51) Int. Cl.
| | | |
|---|---|---|
| *G01N 30/86* | (2006.01) | |
| *G01N 30/72* | (2006.01) | |
| *G01N 33/28* | (2006.01) | |
| *G16C 10/00* | (2019.01) | |
| *G16C 20/70* | (2019.01) | |

(52) U.S. Cl.
CPC ......... *G16C 10/00* (2019.02); *G01N 30/7206* (2013.01); *G01N 30/8693* (2013.01); *G01N 33/28* (2013.01); *G16C 20/70* (2019.02)

(58) Field of Classification Search
None
See application file for complete search history.

(56) References Cited

U.S. PATENT DOCUMENTS

2018/0307803 A1* 10/2018 Watanasiri ............. G16C 20/30

FOREIGN PATENT DOCUMENTS

| CA | 2414873 | * | 1/2002 | ......... G01N 30/8624 |
| WO | WO 2013/121204 | * | 8/2013 | ............. G01N 30/00 |

OTHER PUBLICATIONS

Jones S et al. "Process Design and Economics for the Conversion of Algal Biomass to Hydrocarbons: Whole Algae Hydrothermal Liquefaction and Upgrading", Pacific Northwest National Laboratory. U.S. Department of Energy: PNNL-23227. Mar. 2014.
Mark M. Wright et al. "Techno-Economic Analysis of Biomass Fast Pyrolysis to Transportation Fuels". National Renewable Energy Laboratory: Technical Report: NREL/TP-6A20-46586. Nov. 2010.

(Continued)

*Primary Examiner* — Daniel S Larkin
(74) *Attorney, Agent, or Firm* — Harness, Dickey & Pierce, P.L.C.

(57) ABSTRACT

The present invention relates to a method for reducing the complexity of bio-crudes. The method includes (a) obtaining experimental data of quantitative and qualitative analyses for the bio-crudes, (b) grouping compounds contained in the bio-crudes according to a predetermined basis based on the experimental data, (c) selecting representative compounds from among the compounds belonging to the same group, and (d) reconstituting the bio-crudes as a mixture of the representative compounds.

3 Claims, 6 Drawing Sheets

(56) References Cited

OTHER PUBLICATIONS

Mobolaji Shemfe et al. "Techno-Economic Analysis of Biofuel Production via Biooil Zeolite Upgrading: An evaluation of two catalyst regeneration systems". Biomass Bioenergy 98. 2017. p. 182-193.

Jens F, Peters. "A Kinetic Reaction Model for Biomass Pyrolysis Processes in Aspen Plus". Applied Energy, vol. 188. Science Direct. Feb. 15, 2017, p. 595-603.

Davide Bonalumi. "Preliminary Study of Pyrolysis and Gasification of Biomass and Thermosetting Resins for Energy Production". Energy Procedia 101. Science Direct. Sep. 2016. p. 432-439.

Pedro L. Cruz et al. "Modelling of Co-processing of HDO-oil with VGO in a FCC unit". Fuel, vol. 196. Science Direct. May 15, 2017, p. 362-370. https://doi.org/10.1016/j.fuel.2017.01.112.

Jae Hyung Choi et al. "Effects of Water-Washing Saccharina Japonica on Fast Pyrolysis in a Bubbling Fluidized-bed Reactor". Biomass Bioenergy, vol. 98. Mar. 2017. p. 112-123.

Hoang Vu Ly et al. "Fast Pyrolysis of *Saccharina japonica* Alga in a Fixed-bed Reactor for Bio-oil Production". Energy Conversion and Management 122. Science Direct. Aug. 2016. p. 526-534.

Hoang Vu LY et al. "Fast Pyrolysis of Macroalga *Saccharina japonica* in a Bubbling Fluidized-bed Reactor for Bio-oil Production". Energy 93. Science Direct. Dec. 2015. p. 1436-1446.

\* cited by examiner

METHOD OF SIMULTANEOUS MODELING AND COMPLEXITY REDUCTION OF BIO-CRUDES FOR PROCESS SIMULATION

CROSS-REFERENCE TO RELATED APPLICATIONS

The present application claims priority under 35 U.S.C. § 119 to Korean Patent Application No. 10-2018-0060659, filed on May 28, 2018, in the Korean Intellectual Property Office, the entire contents of which are hereby incorporated by reference.

BACKGROUND OF THE INVENTION

1. Field of the Invention

The present invention relates to a method for reducing the complexity of bio-crudes generated using thermochemical conversion of biomass. More particularly, the present invention relates to a method for reducing complexity by minimizing the number of major constituent compounds so that bio-crudes containing hundreds of compounds are efficiently handled using a process simulator.

2. Description of the Related Art

In the last two decades, studies on biofuel with the goal of replacing fossil fuels have gradually intensified. In comparison to crude oil, biological feedstocks for biofuel production, that is, biomass, are globally available.

Among them, biofuel production using crops entails several disadvantages, which presents obstacles to the use of biofuels as a fossil-fuel energy alternative. As one thereof, opponents of biofuels argue that large government incentives for the development of crops and production sites led to the so-called "biofuel boom", which peaked in 2005 and subsequently led to a rise in global food prices.

Second-generation biomass such as lignocellulosic or agricultural residues has emerged in order to avoid the problems of grain-based biomass. In recent years, concerns about aquatic biomass, that is, microalgae and macroalgae, as third-generation biomass have been increased.

There are three general routes for the conversion of biomass (biological, chemical, and thermochemical routes). Each has its own set of advantages and disadvantages, which depend on several factors such as the type of biomass, available resources, and location.

Among them, a thermochemical process offers the most direct conversion. Furthermore, the product phase distribution and composition may be adjusted by changing process variables such as temperatures, pressure, and heating rates. Finally, the thermochemical process may be performed in a continuous mode, unlike biochemical processes, which is an important advantage in terms of economics and energy savings compared to batch processes.

Meanwhile, accurate process simulation related to the thermochemical conversion of biomass, such as pyrolysis or hydrothermal liquefaction, is challenging due to the complex nature of the products. The pyrolysis process yields products in all three phases (gas, liquid, and solid). The goal of pyrolysis is to maximize the yield of the liquid phase since the desired final products are liquid fuels. Pyrolysis liquid products, that is, bio-crudes, are a complex organic mixture containing hundreds of compounds. The compounds are mostly oxygenated hydrocarbons, organic acids, and other organics with varying molecular masses and boiling points. Furthermore, bio-crudes, especially those produced from aquatic biomass, contain a comparatively large water content. Organic compounds are completely solvated, semi-solvated, or non-solvated in water, and form a two-phase liquid (lipophilic liquid and hydrophilic liquid) with gradual phase transition.

Therefore, one of the common issues in the process simulation of bio-crudes is defining a mixture containing the minimum number of compounds, which, in all respects (physical, chemical, and thermodynamic properties such as a chemical composition, a density, and a heating value), accurately represent the complex bio-crude mixture. The mixture containing the reduced number of compounds representing the liquid product together with products from other phases must be in atomic mass balance with the feedstocks.

One approach to these challenges is modeling the pyrolysis kinetics using key biopolymer components. Although this approach possesses predictive capabilities, it lacks a built-in strategy for minimizing constituent compounds and does not fully employ experimental data obtained by analyzing product characterization.

Another approach to bio-crude modeling was proposed by Jones et al. and Bonalumi, in which a set of pseudocomponents is defined from the available constituent compounds in the process simulator's mass database and in which manual mixing and matching is performed to thus adjust the properties of the reduced mixture to reflect those of original bio-crudes. This may reduce the time required to constitute the reduced mixture, but usually results in considerably reduced accuracy.

Furthermore, a similar approach was proposed by Cruz et al., in which real constituent components experimentally found in bio-crudes and pseudo-constituent components are combined in order to reproduce the true boiling point (TBP) curve of the bio-crudes. In this research, the pseudo-constituent components are added to the simulated mixture or are generated by a process simulator in order to manually tune the properties of the mixture containing a set of constituent compounds not experimentally found in the bio-crudes. Although some real constituent components are used, the total number of constituent components, that is, compounds, of the reduced mixture is large, namely 47, of which 40 are pseudo-constituent components.

In summary, since the experimental data are not fully exploited, all of the above-mentioned conventional approaches introduce artifacts and biases that are not negligible in process simulations, in some cases, the results are different from each other, and the conventional approaches are applicable only to fewer types of biomass and conversion processes.

CITATION LIST

Non-Patent Literature (Non-Patent Document 1) Jones S, Zhu Y, Anderson D, Hallen R T, Elliott D C. Process design and economics for the conversion of algal biomass to hydrocarbons: whole algae hydrothermal liquefaction and upgrading; 2014.

(Non-Patent Document 2) Wright M M, Ja Satrio, Brown R C, Daugaard D E, Hsu D D. Techno-economic analysis of biomass fast pyrolysis to transportation fuels. Nat'l Renew. Energy Lab 2010; 89:S2-10.

(Non-Patent Document 3) Shemfe M, Gu S, Fidalgo B. Techno-economic analysis of biofuel production via biooil zeolite upgrading: an evaluation of two catalyst regeneration systems. Biomass Bioenergy 2017; 98:182-93.

(Non-Patent Document 4) Peters J F, Banks S W, Bridgwater A V, Dufour J. A kinetic reaction model for biomass pyrolysis processes in Aspen Plus. Appl. Energy 2017; 188:595-603.

(Non-Patent Document 5) Bonalumi D. Preliminary study of pyrolysis and gasification of biomass and thermosetting resins for energy production. Energy Proc 2016; 101:432-9.

(Non-Patent Document 6) Cruz P L, Montero E, Dufour J. Modelling of co-processing of HDO-oil with VGO in a FCC unit. Fuel 2017; 196:362-70.

(Non-Patent Document 7) Choi J H, Kim S S, Ly H V, Kim J, Woo H C. Effects of water-washing *Saccharina japonica* on fast pyrolysis in a bubbling fluidized-bed reactor. Biomass Bioenergy 2017; 98:112-23.

(Non-Patent Document 8) Ly H V, Kim S S, Choi J H, Woo H C, Kim J. Fast pyrolysis of *Saccharina japonica* alga in a fixed-bed reactor for bio-oil production. Energy Convers. Manag. 2016; 122:526-34.

(Non-Patent Document 9) Ly H V, Kim S S, Woo H C, Choi J H, Suh D J, Kim J. Fast pyrolysis of macroalga *Saccharina japonica* in a bubbling fluidized-bed reactor for bio-oil production. Energy 2015; 93:1436-46.

SUMMARY OF THE INVENTION

Accordingly, the present invention has been made keeping in mind the above problems occurring in the related art, and an object of the present invention is to provide a method for reducing the complexity of bio-crudes. In the method, the number of constituent compounds of bio-crudes is minimized, and physical, chemical, and thermodynamic properties of the bio-crudes are accurately represented using only experimental data, thereby enabling accurate and efficient bio-crude process simulation.

In the description of the present invention, detailed descriptions of related known techniques or configurations incorporated herein will be omitted when the same may make the gist of the present invention unclear.

The embodiments according to the concept of the present invention can be variously changed and have various forms, so that specific embodiments are illustrated in the drawings and described in detail in this specification or application. However, the following description does not limit the embodiments according to the concepts of the present invention to any particular mode of disclosure, and should be understood to include all variations, equivalents or alternatives falling within the spirit and scope of the present invention.

The terminology used herein is for the purpose of describing particular embodiments only and is not intended to be limiting of the present invention. As used herein, the singular forms are intended to include the plural forms as well, unless the context clearly indicates otherwise. It will be further understood that the terms "comprise", "include", "have", etc. when used in this specification specify the presence of stated features, integers, steps, operations, elements, components, or combinations thereof, but do not preclude the presence or addition of one or more other features, integers, steps, operations, elements, components, or combinations thereof.

In order to accomplish the above object, the present invention provides a method for reducing the complexity of bio-crudes, the method including (a) obtaining experimental data of quantitative and qualitative analyses for the bio-crudes, (b) grouping compounds contained in the bio-crudes according to a predetermined basis based on the experimental data, (c) selecting representative compounds from among the compounds belonging to the same group, and (d) reconstituting the bio-crudes as a mixture of the representative compounds.

The case where experimental data provided to the method for reducing the complexity of the bio-crudes according to the present invention are obtained using gas chromatography/mass spectrometry (GC-MS) will be described below as an example.

First, the experimental data of the quantitative and qualitative analyses are obtained using gas chromatography/mass spectrometry (GC-MS) in step (a).

Subsequently, among the analysis results obtained using GC-MS, the chemical group and the retention time of the compounds constituting the bio-crudes and the type of atoms contained in the compounds are selected as classification bases, thus grouping the compounds contained in the bio-crudes in step (b).

Specifically, step (b) includes (b-1) classifying compounds contained in crude oil according to chemical group (for example, aliphatic compounds and aromatic compounds) and performing first grouping into upper groups, (b-2) classifying the compounds in the same upper group according to a retention time and performing second grouping into middle groups, and (b-3) classifying the compounds in the same middle group according to the type of atoms contained in the compounds and performing third grouping into subgroups.

The classification according to the type of the atoms contained in the compounds in step (b-3) means that the compounds in each middle group are reclassified into subgroups according to a molecular formula.

For example, the third grouping may be performed into any one subgroup among a first subgroup (including the compound represented by $C_vH_w$), a second subgroup (including the compound represented by $C_vH_wO_x$), a third subgroup (including the compound represented by $C_vH_wN_y$ or $C_vH_wO_xN_y$), and a fourth subgroup (including the compound represented by $C_vH_wS_z$, $C_vH_wO_xS_z$, or $C_vH_wO_xN_yS_z$) according to the type of atoms contained in the compounds belonging to a particular middle group (v, w, x, y, and z are positive integers).

Subsequently, step (c) includes selecting a representative compound to be finally contained in the bio-crude mixture including the reduced number of constituent compounds.

Among the compounds in each subgroup, the compound having the largest peak area on a normalized GC-MS chromatogram is selected as the representative compound.

Next, step (d) includes reconstituting a mixture which includes only the representative compounds so that a reduced number of constituent compounds is included compared to the original bio-crude mixture and which has substantially the same physical properties as the original bio-crude mixture.

That is, in this step, the peaks of compounds other than the representative compound for each subgroup are removed on the normalized GC-MS chromatogram, and the areas of the removed peaks are added to the peak of the representative compound. The compound represented by the normalized GC-MS chromatogram obtained as described above is a mixture which includes a reduced number of finally obtained compounds to be provided to the process simulation according to the present invention.

According to the method for reducing the complexity of the bio-crudes, a mixture containing the reduced number of compounds can be used as input data in process simulation of bio-crudes, thereby achieving accurate and efficient process simulation of the bio-crudes.

According to the method for reducing the complexity of the bio-crudes for the process simulation according to the present invention, the number of constituent compounds of the bio-crudes can be minimized and the physical properties of the original bio-crudes can be accurately represented using only the experimental data obtained using GC-MS, thereby enabling accurate and efficient process simulation of the bio-crudes.

Further, although the method according to the present invention can be performed manually, full automation of the method is also feasible. When full automation is performed, work requiring several hours when manual operation is performed can be finished in a few minutes, and the results are outputted in a form that can be directly used in a process simulator. Accordingly, it is possible to provide a user-friendly environment.

Therefore, considering that the use of a process simulator is essential for designing a new renewable energy production process, the present invention has great advantages, including a wide range of applicability, excellent ease of use, and complete automation.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, the present invention will be described in more detail with reference to Examples.

The Examples presented are only specific Examples of the present invention and are not intended to limit the scope of the present invention.

Example

1. Experimental Techniques
1.1. Pyrolysis Process

The method for reducing the complexity of bio-crudes according to the present invention was tested on seven datasets, originating from studies published in the above non-patent documents 7 to 9.

That is, the brown macroalga *Saccharina japonica* was subjected to a pyrolysis process in fixed- and fluidized-bed reactors under various process conditions (temperature, heating rate, fluidizing velocity, and so on) according to the pyrolysis process conditions of the following Table 1 (experimental pyrolysis conditions). The effect of different pre-treatment routes, such as water washing and acid washing, was also reported. The optimal condition (maximum liquid yield) for each reactor type and pre-treatment was determined. The proximate and ultimate analyses of marine algae were performed, thus providing information on the elemental composition, moisture content (after drying), and mineral content. The ultimate analysis was also used to characterize the solid product of pyrolysis (bio-char). Properties of bio-crudes and gases were analyzed using gas chromatography/mass spectrometry (GC-MS). The ultimate analysis was finally performed on two phases of bio-crudes (organic and aqueous phases) and the moisture content thereof was determined. The higher heating values (HHV) of the feedstocks and bio-crudes were calculated using models by Channiwala et al. and Dulong-Bertolet, respectively. The same models were used for HHV calculation of the simulated bio-crudes.

1.2. Gas Chromatography/Mass Spectrometry (GC-MS)

The properties of the bio-crudes and gases were analyzed using an Agilent 7890A GC-MS (Agilent Technologies, Santa Clara, Calif., United States) having a HP-5MS capillary column (30 m, 0.25 mm, 0.25 mm). High-purity helium was used as a carrier gas at a flow rate of 1.0 mL/min. The temperature of the GC injector having an injection volume of 1 mL was kept at 280° C. The initial temperature of the GC oven was maintained at 40° C. for 1 min, and was programmed so that the temperature was increased from 40° C. to 300° C. at a heating rate of 15° C./min. Subsequently, the oven was maintained at a final temperature for 5 min. Identification of the chromatographic peaks for the bio-oil components was based on an automatic library search (Wiley 9th/NIST08 library). Accuracy greater than 80% was used as a threshold value for identification.

2. Method for Reducing Complexity of Bio-Crudes
2.1. Key Concepts of Reduction

Raw experimental data obtained through GC-MS analysis are the core of the reduction method according to the present invention. GC-MS analysis provides the International Union of Pure and Applied Chemistry (IUPAC) names, retention times (min), normalized peak areas (%), and chemical groups of compounds. Boiling points (BP) and CAS (chemical abstract service) numbers were taken from external document sources (Chemical Abstracts Service, Columbus, Ohio, USA).

The objective of the reduction method is maximizing the reduction of the number of constituent compounds of the original mixture (bio-crudes) and minimizing the difference between key parameters that are used to compare the bio-crudes and the reduced mixture. The key parameters chosen to compare the characteristics and adjust the level of reduction between the original and reduced mixtures are (i) relative ratios of compounds in specific chemical groups, (ii) weighted averages of molecular masses (MM) of chemical groups, (iii) weighted averages of boiling points (BP) of chemical groups, and (iv) total atomic weights of all chemical groups within a single phase.

The relative ratio $X_i$ of a single compound in the mixture was calculated using the following equation:

$$X_i = A_i \bigg/ \sum_{i=1}^{n} A_i \tag{1}$$

where $A_i$ is the normalized peak area of compound i.

The relative ratio of components in a specific chemical group in the mixture is the sum of Xs for every component that belongs to the same chemical group. The weighted MM and weighted BP of the single component in the mixture $MM_{WA,i}$ and $BP_{WA,i}$ were calculated by:

$$MM_{WA,i} = X_i MM_i [\text{kg kmol}^{-1}] \tag{2}$$

$$BP_{WA,i} = X_i BP_i [^\circ C.] \tag{3}$$

The weighted average MM and BP of the chemical group $MM_{WA,gr,n}$ and $BP_{WA,gr,n}$ were calculated using:

$$MM_{WA,gr,n} = \sum_{i=1}^{n} MM_{WA}(i) \bigg/ \sum_{i=1}^{n} X_i [\text{kg kmol}^{-1}] \tag{4}$$

$$BP_{WA,gr,n} = \sum_{i=1}^{n} BP_{WA}(i) \bigg/ \sum_{i=1}^{n} X_i [^\circ C.] \tag{5}$$

The mass of the single compound $m_i$ (kg) in the mixture (phase) was calculated according to:

$$m_i = m_{feed} \times X_i \times \gamma_{liq} (1 - \varphi_{H2O}) \tag{6}$$

where $m_{feed}$ (kg) is the chosen mass of the feed material, $\gamma_{liq}$ is the experimentally determined mass yield of the organic or aqueous phase in the liquid product, and $\varphi_{H2O}$ is the experimentally determined water content of the corresponding phase.

First, the weighted average MM and weighted average BP were calculated for chemical groups of all components from raw GC-MS data. The distribution of compounds to different chemical groups depends on the user's definition. The total atomic weight (C, H, N, O; kmol) of the entire mixture was calculated using the sum of relative contribution amounts from every component in the mixture. Subsequently, the constituent compounds belonging to the same chemical group were identified and classified into subgroups using a threshold retention time value for discrimination thereof. The threshold retention time for each chemical group was optimized using a genetic algorithm for the minimum number of compounds in a mixture using the maximum absolute difference of weighted average MM and weighted average BP as a constraint function. The maximum BP absolute difference of 30° C. was taken as a limit at which the constituent compounds of the same chemical group are distributed into different subgroups of the chemical group.

Finally, the number of the constituent compounds that were considered to be structurally similar to each other was reduced. The component having the largest normalized peak area was taken as a representative component for a subgroup and other components were removed. The value of the normalized peak area of the removed constituent compounds was then added to the normalized peak area of the remaining constituent compound, thus increasing the area. This was applied to all chemical groups in the mixture, whereby the total number of components was reduced while the aforementioned key parameters were not considerably changed compared to the raw data.

2.2. Reactor Balance

Figure 1:
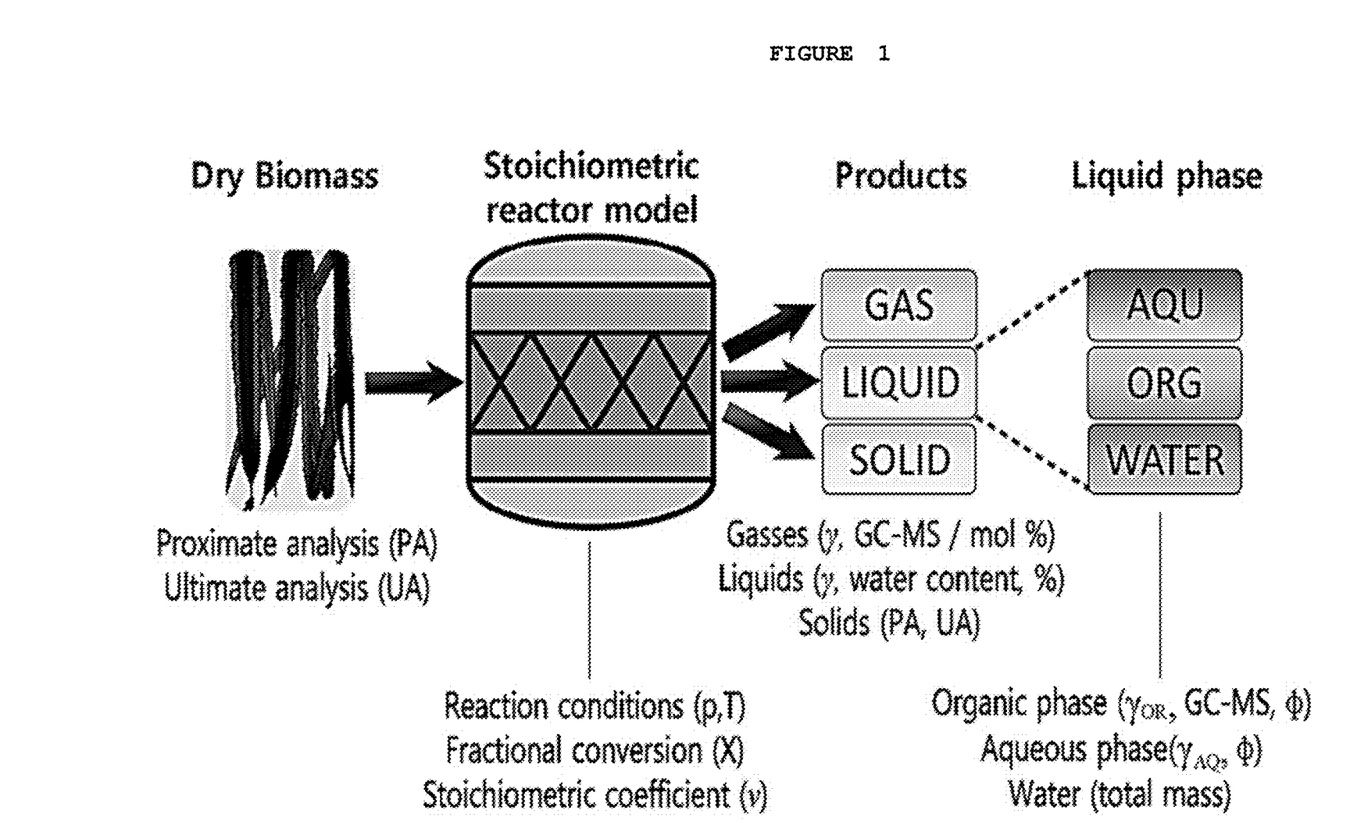
FIG. 1 is a mimetic view showing relevant experimental data for fitting a balance of a pyrolysis reaction furnace in an embodiment of the present application, wherein γ represents a mass yield (mol %), ϕ represents a moisture content (wt %), AQU represents the aqueous phase of a mixture, and ORG represents the organic phase of the mixture.

In order to use the results of the reduction method in process simulation, the reduced liquid mixture, along with generated water, gases, and solids (char), need to be in a mass-balance state with feedstocks (feed material). First, the total amount of each element from the feedstocks is calculated. To this end, the proximate analysis (PA) and the ultimate analysis (UA) of the feedstocks are used (FIG. 1). In the present embodiment, the main elements involved in the pyrolysis process were carbon, hydrogen, oxygen, and nitrogen. The equation for calculating the total atomic weight of the feedstocks and the product is presented below with respect to carbon and hydrogen. The total amount of carbon in the feedstocks ($n(C)_F$) is calculated according to:

$$n(C)_F = \frac{\left(m_{feed} \times \frac{(VM + FC) \times W_C}{100}\right)}{MM(C)} [\text{kmol}] \tag{7}$$

where VM, FC, and Wc represent the wt % of volatile matter, fixed carbon, and total carbon content, respectively.

The moisture (water) content of the feed material was considered when calculating the amount of oxygen and hydrogen. Hence, the equation for the total hydrogen content in the feed material ($n(H)_F$) differs from Equation (7) and is defined as:

$$n(H)_F = \frac{\left(m_{feed} \times \frac{(VM + FC) \times W_H}{100}\right)}{MM(H)} + N(H)_{wat.} \left(\frac{m_{feed} \times \frac{MS}{100}}{MM(H_2O)}\right) [\text{kmol}] \tag{8}$$

where $W_H$ is the total hydrogen content (wt %), $N(H)_{wat.}$ is the number of hydrogen atoms in water, and MS represents moisture content (wt %). The mineral content (ASH) is calculated using the ASH content in the PA, and this forms a constituent element of the solid product. The total carbon content in the product ($n(C)_P$) is the sum of the carbon amounts in all of the product phases (FIG. 1). This means the content of carbon in all of the carbon-containing components in the liquid phases ($n(C)_{liq}$), carbon-containing gases ($n(C)_{gas}$), and the solid phase as represented in the following equations:

$$n(C)_P = n(C)_{liq} + n(C)_{gas} + n(C)_{solid} [\text{kmol}] \tag{9}$$

$$n(C)_{liq,i} = \frac{m_i}{MM_i} \times N(C)_i [\text{kmol}] \tag{10}$$

$$n(C)_{liq} = \sum_{i=1}^{n} n(C)_{liq,i} [\text{kmol}] \tag{11}$$

where $n(C)_{liq,i}$ is the amount of carbon from the single component i of the liquid phase (organic and aqueous phases). $m_i$ is the mass of the constituent compound i as defined in Equation (4). $MM_i$ is the molecular mass of the constituent compound i, and $N(C)_i$ is the number of carbon atoms of the constituent compound i.

The hydrogen amount from the liquid phase is calculated similarly, except for hydrogen from moisture ($n(H)_{H2O}$) and reaction water (one of the components of the liquid product phase), which must be considered in the total balance, using the following equations.

$$n(H)_{liq} = \sum_{i=1}^{n} n(H)_{liq,i} + n(H)_{H_2O} [kmol] \quad (12)$$

$$n(H)_{H_2O} = \frac{m_{feed} \times \gamma_{liq.ph.} \times \varphi_{H_2O}}{MM(H_2O)} \times N(H)_{H_2O} [kmol] \quad (13)$$

Since carbon dioxide ($CO_2$) was the most prevalent carbon-containing component in the gas phase, carbon dioxide was used as a calculation example. The carbon amount thereof ($n(C)CO_2$) was calculated using the following equation:

$$n(C)_{CO_2} = \frac{m_{feed} \times \gamma_{gasph.} \times \gamma_{CO_2}}{MM(CO_2)} \times N(C)_{CO_2} [kmol] \quad (14)$$

where $\gamma_{gasph.}$ and $\gamma_{CO2}$ are mass yields of the gas phase and carbon dioxide, respectively, and $N(C)_{CO2}$ equates to the number of carbon atoms in the constituent compounds. Similarly, the carbon amounts for other gas-phase constituent compounds, as well as other atomic weights, were calculated.

Finally, the carbon amount ($n(C)_{char}$) from the solid product calculated from the UA of the bio-char on an ash-free basis was calculated according to the following equation:

$$n(C)_{char} = \frac{\left(m_{feed} \times \gamma_{solidph.} - m_{feed} \times \frac{ASH}{100}\right) \times \left(\frac{W_{C,char}}{100}\right)}{MM(C)} [kmol] \quad (15)$$

where ASH is the mineral content (wt %) from PA of the raw material, $n(C)_{char}$ is the mass yield of the solid phase (char), and $W(C)_{char}$ is the mass fraction of carbon in char (wt %).

For the purpose of process simulation, balance is achieved when the difference between the total amount of atoms in the product and the total amount of atoms in the feedstocks is less than one. When the above-mentioned condition is not the initial condition, the compositions of the char and the gas in the product are changed. Non-linear constrained numerical optimization using the interior-point algorithm was used to achieve this. Boundaries for optimization were set based on the composition within experimentally determined limits (the minimum and maximum between all considered datasets) (Table 2 (variables of the reduction method and limits thereof)), and the constraint was the law of mass conservation. The constraint is that the sum of the mass fractions of gas components and the sum of the atomic fractions of char must each be 100.

TABLE 1

| # | Pyrolysis temperature/reactor type/pre-treatment |
|---|---|
| 1 | 350° C./fluidized bed/water-washed |
| 2 | 375° C./fluidized bed/water-washed |
| 3 | 400° C./fluidized bed/water-washed |
| 4 | 425° C./fluidized bed/water-washed |
| 5 | 450° C./fluidized bed/water-washed |
| 6 | 375° C./fluidized bed/no pre-treatment |
| 7 | 450° C./fixed bed/acid-washed |

TABLE 2

| Component | Minimum | Maximum |
|---|---|---|
| Gas components | | |
| CO | 7 | 11 |
| $CO_2$ | 85 | 91 |
| $H_2$ | 0.01 | 0.5 |
| $CH_4$ | 0.1 | 3.2 |
| $C_2H_4$ | 0.01 | 0.7 |
| $C_2H_5$ | 0.1 | 2 |
| $C_3H_8$ | 0.1 | 1.5 |
| $C_4H_{10}$ | 0.1 | 0.7 |
| Char atomic fractions | | |
| C | 28 | 45 |
| H | 1.5 | 4 |
| O | 45 | 70 |
| N | 0.5 | 3 |

* All the values expressed in wt. %. Atomic fractions of char are on ash-free basis.

2.3. Reduction Method Automation

The reduction method and reactor balance calculations were automated in the form of a specialized program using MATLAB 2017a (Mathworks, Sherborn, Mass., USA).

Figure 2:
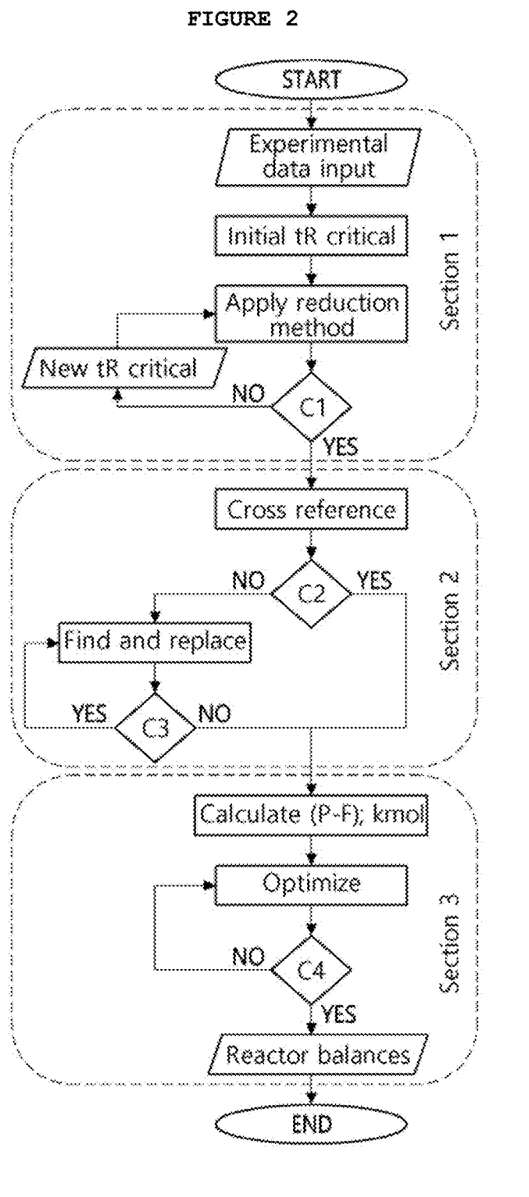
FIG. 2 is a flow diagram showing an automated reduction method according to the embodiment of the present application.

The program may be divided into three main sections (FIG. 2). Section 1 of the program represents the reduction method. The reduced mixture may contain constituent compounds that cannot be found in the material database of the process simulator. However, the database contains compounds which are chemically similar to each other. Accordingly, Section 2 of the program cross-references the database and the reduced mixture is subjected to necessary replacement operations if needed. Finally, in Section 3, the reactor balance is optimized. To get started, experimental data must be inputted in a predetermined form including analyses of the feed materials and products as shown in FIG. 1.

In the program, an initial critical retention time ($t_R$) of 2.5 min is used to thus divide chemical groups in the liquid product phase into subgroups. The reduction method is then performed. When the total number of constituent compounds in the chemical group is minimized within the constraints (FIG. 2, Table 3 (summary of conditions of the automated reduction method); C1), this method is deemed to be converged.

The constraints of the present method are defined as:

$$|Y_{WA,red} - Y_{WA,exp}| \leq C \quad (16)$$

where $Y_{WA,red}$, and $Y_{WA,exp.}$ are the weighted averages of chemical groups BP and MM for the reduced mixture and the original (experimental) mixture, respectively.

Constraints for MM and BP used in Examples were 15 kgkmol$^{-1}$ and 30° C. When the first condition is met, the program cross-references compounds. If the compound from the reduced mixture is not present in the material database of the process simulator, the program finds the most analogous compound from the database based on the number of atoms and the minimum value of the Euclidian distance of BP and MM.

If the third condition is met (Table 3), the program may generate a mixture including the minimum number of constituent compounds, all of which are contained in the database of process simulation software, and may proceed to the final section.

The program performs calculations and optimizes the resulting mixture as described in the subsection 'reactor balance'. When the condition C4 is met, the program generates the results in a predetermined form.

TABLE 3

| Condition | Condition description |
| --- | --- |
| C1 | Converged? Max critical $t_R$ for minimum number of compounds in reduced mixture; CONSTRAINT: weighted average molecular masses and boiling points differences between reduced mixture compounds and original compounds |
| C2 | Is the compound in the database? |
| C3 | Are the absolute differences of reduced and replaced mixture's weighted average MM and BP greater than the criteria? |
| C4 | Are the differences of atomic amounts from product and feed <1? |

2.4. Reduction Method Performance Evaluation and Validation 2.4.1. Performance Evaluation In order to evaluate the performance of the reduction method, a reduction factor was introduced as an index. The reduction factor is defined as the ratio of the total number of constituent compounds in the organic and aqueous phases identified using GC-MS and the total number of constituent compounds in the reduced mixture. A calculation time was measured using the built-in MATLAB function cputime.

2.4.2. Method Validation

The results of the program (reduced mixtures and reactor balances) were validated by a simulation in Aspen Plus 10 (Aspen Tech, Cambridge, Mass., USA) at a scale of 100 t/h of dry algae. The process simulation is depicted using a process flow diagram (PFD) (FIG. 3) divided into three segments. Each segment depends on a property method, which is a unifying set of properties and models specifically designed for a particular part within the process.

Figure 3:
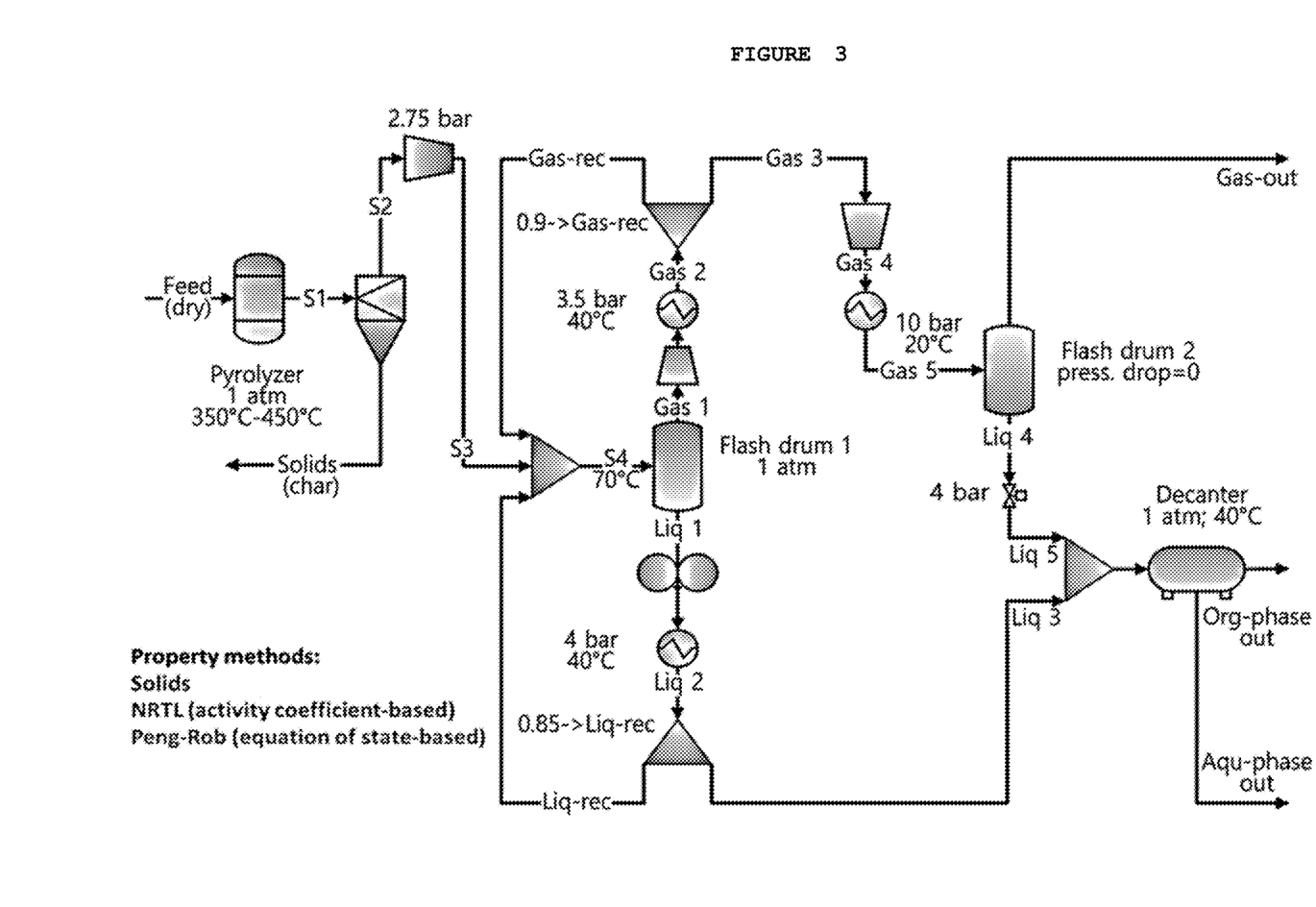
FIG. 3 is a flow diagram showing pyrolysis and separation processes according to the embodiment of the present application.

A red segment represents the separation of solid products using a pyrolysis reactor (stoichiometric reactor model) and a cyclone.

The property method used in this segment is specifically designed for the processing of solids and is generally used for coal processing, pyro-metallurgical processes, and polymer and starch processing. Macroalgae feeds and the solid product (char) are both defined as nonconventional solids using experimental PA and UA. According to the dataset, the number of chemical reactions in the reactor model ranged from 25 to 28, encompassing the products of all phases. The chemical reaction for conventional gaseous and liquid constituent components generated due to the pyrolysis of non-conventional solids is defined by:

$$(-v_i) \times \text{FEED} \rightarrow 1 \times PROD_i; \ X_i = \frac{m(PROD_i)}{m(\text{FEED})} \quad (17)$$

where $-v_i$ is a stoichiometric coefficient for the FEED when component $PROD_i$ is generated and is equal in numerical value to the molecular mass of the constituent compound of the product. The fractional conversion factor $X_i$ for the constituent compound i is calculated by the program for each constituent compound of the product. The chemical reaction for nonconventional solid components (char) is defined similarly to other components, except for the stoichiometric coefficient (1) of the feed materials. The PA and UA values for char are calculated using the program, and the data must be inputted into the reaction furnace model.

The blue segment represents the quenching and the separation of the aqueous phase from non-water-soluble components and light gases. Due to the large water content and strongly non-ideal solutions, the activity-coefficient-based property method is used in this segment (Non-random two-liquid, NRTL). After a first flash drum, both the vapor and liquid phases are compressed, transported at a pressure of 3.5 to 4 bar, and cooled to 40° C. (FIG. 3, streams GAS 2 and LIQ 2). The recycled stream fraction was set to 0.85 and 0.9 for the liquid and vapor phases, respectively.

The best separation was achieved when the supplied feed material was cooled to below 80° C. and partially condensed by quenching with chilled recycled streams. The vapor phase moved to a green segment is first pressurized to 10 bar and cooled to 20° C. (FIG. 3, stream GAS 5). A second flash drum separates light gases from liquids, which are then released from a pressurized system to a pressure of 4 bar (FIG. 3, stream LIQ 5) and supplied to a liquid-liquid separator (Decanter model). Further, the aqueous stream LIQ3 represents materials fed into a decanter for recovery of residual organic compounds. Due to the major presence of oxygenated hydrocarbon compounds, in the green segment, a Peng-Robinson equation is used as a state property method. Streams ORG-PHASE OUT and S2 at 25° C. and 1 atm (total liquid), representing the organic phase and the bio-crudes, respectively, were taken as points of comparison with experimental data.

2.4.3. Data Analysis

In order to test the statistical significance of the difference between the experimental and simulated data, a two-sample t-test and a one-way analysis of variance (one-way ANOVA) Tukey's test were used as additional means of validation. All of the statistical hypotheses were tested at a significance level of 95% ($\alpha=0.05$).

Statistical analysis was performed in OriginPro 2017 on a personal computer equipped with an AMD A8-7650 K Radeon R7 processor of 3.30 GHz, 14 computing cores (8 CPU, 6 GPU), and 8 GB (6.94 GB usable) of RAM, and the reduction method automation was performed in MATLAB 2017a.

3. Result 3.1. Reduction Evaluation Parameters

As can be observed from Table 4 (evaluation of the performance of the reduction method), the program reduced seven mixtures by 2.6 times or more, and the maximum reduction factor was 5.5. The average reduction factor based on the observed datasets was 3.7. With respect to the calculation time for the observed datasets, the lowest was 2.8 min and the highest was 5.1 min. The constituent compound distribution over the same retention time is depicted for the organic phase of dataset 3 (FIG. 4).

Figure 4:
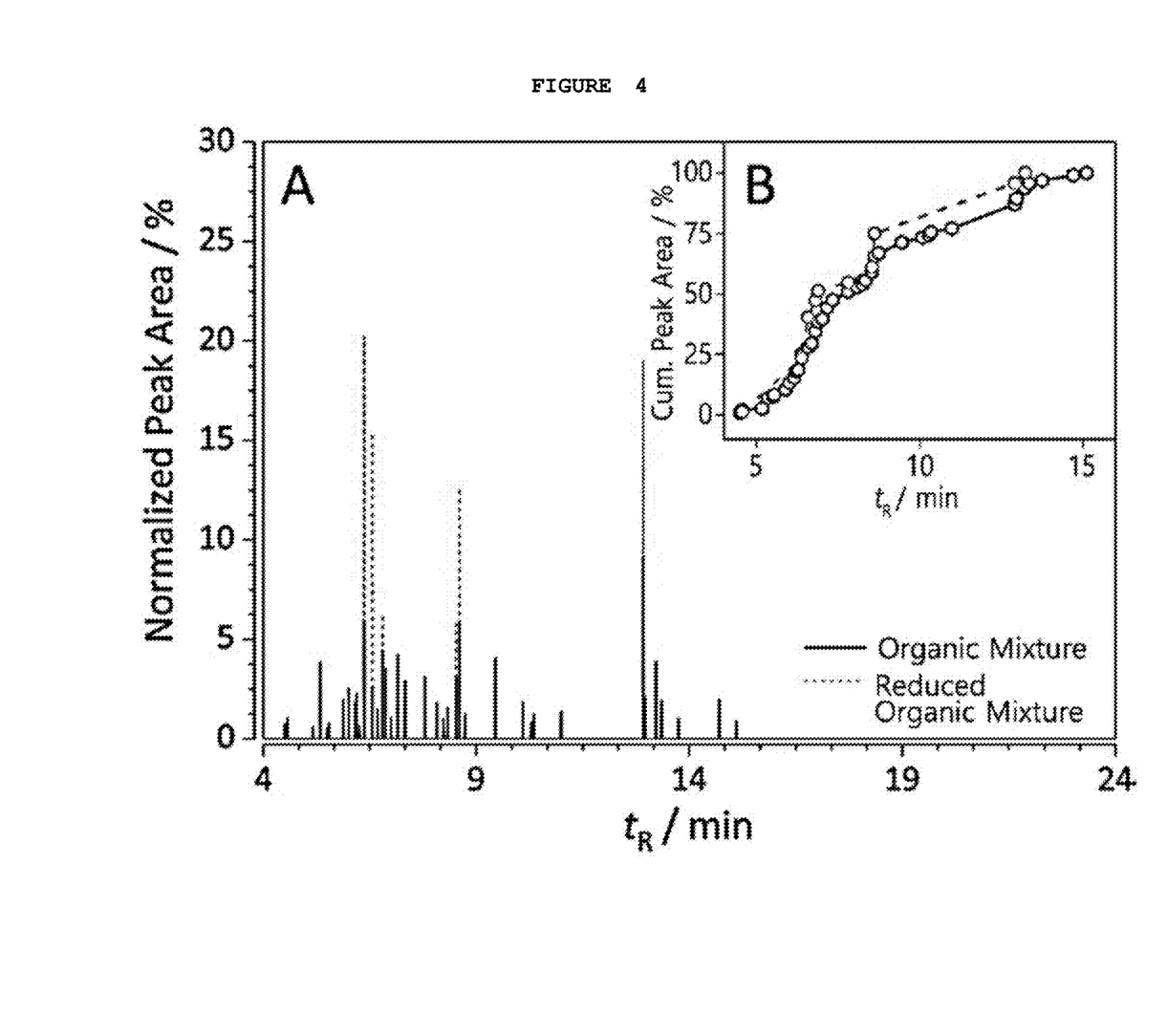
FIG. 4 is a graph showing an exemplary depiction (A) of a normalized GC-MS chromatogram and the comparison (B) of trends of cumulative peak areas with respect to a retention time (the experimental organic phase is represented by a green color (solid line) and the reduced organic phase is represented by an orange color (dotted line))

The total number of constituent compounds is reduced while the normalized peak area is increased in accordance with the reduction method (FIG. 4A). FIG. 4B shows the comparison of trends of cumulative peak areas with respect to increased retention time. The trends are in excellent agreement and are significantly similar (t=0.222; p=0.825>t assuming equal variances; t=0.232; p=0.820>t not assuming equal variances).

TABLE 4

|  | Dataset | | | | | | |
|---|---|---|---|---|---|---|---|
|  | 1 | 2 | 3 | 4 | 5 | 6 | 7 |
| Number of compounds | | | | | | | |
| Experimental | 41 | 48 | 64 | 63 | 58 | 55 | 120 |
| Reduced mixture | 15 | 18 | 15 | 16 | 15 | 17 | 22 |
| Reduction factor | 2.73 | 2.67 | 4.27 | 3.94 | 3.87 | 3.24 | 5.45 |
| Runtime/min | 2.81 | 3.09 | 3.5 | 3.45 | 3.3 | 3.19 | 5.11 |

* Identified using GC-MS.

3.2. Comparison of Product Phase Distribution and Atomic Balance

Figure 5:
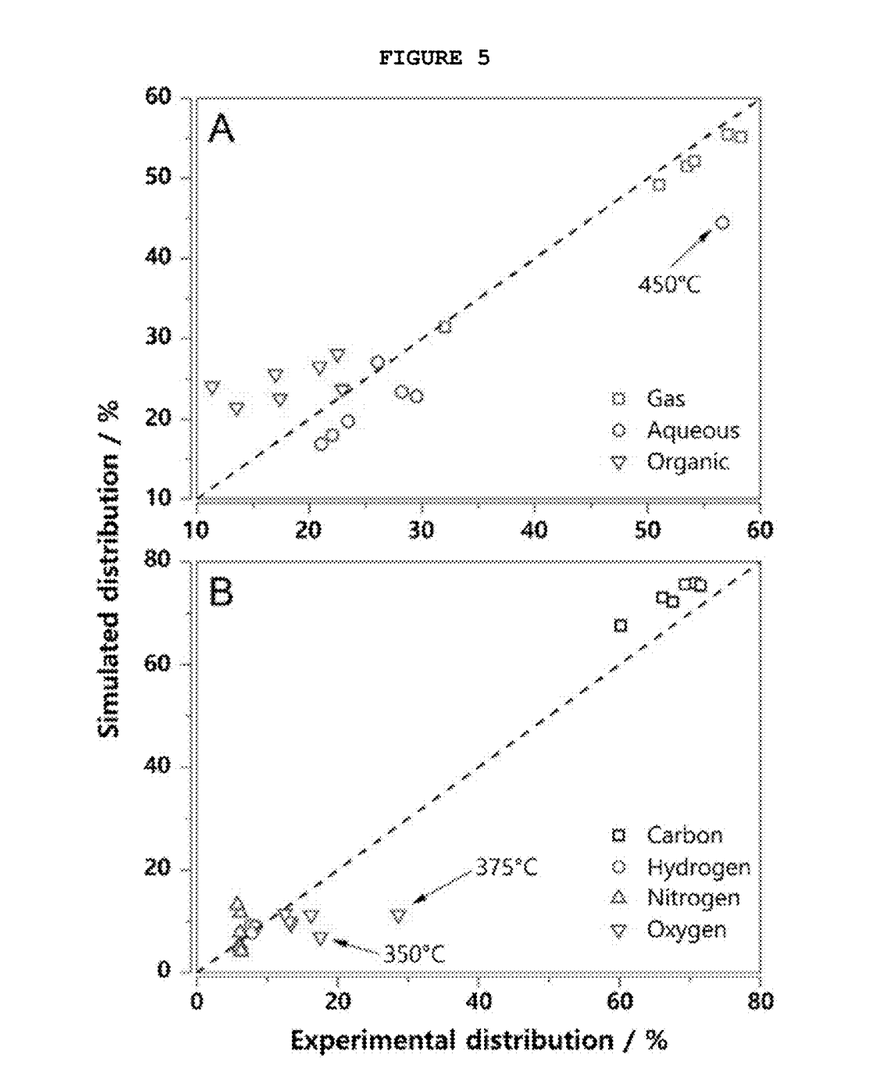
FIG. 5 is a graph showing a comparison result (A) of an experimental value and a simulated value of phase distribution of a product excluding a solid and a comparison result (B) of an experimental value and a simulated value of atomic distribution of an organic phase.

Experimental phase distributions of the organic phase, aqueous phase, and light gases for every dataset were compared with simulated values after the phase separation segment (FIG. 5A). The simulated data closely correspond to the experimental data as the root mean square errors (RMSE) of organic-phase, aqueous-phase, and gas-phase fractions are 7.45%, 6.13%, and 1.87%, respectively. This was identified using ANOVA with the Tukey test, and the difference in use of simulated and experimental values was not significant (p=0.999>α; p=0.890>α; p=0.704>α; α=0.05).

Larger deviations for the aqueous phase (e.g., 450° C., FIG. 5A) are caused by the generation of a larger amount of reaction water from the fixed-bed reactor, unlike the simulation, which cannot provide sensitive reaction. The organic phase was the desired intermediate product of pyrolysis, so the atomic distributions of the organic phases from six datasets were compared with simulated values (experimental atomic distribution for the 7$^{th}$ dataset was not available).

From FIG. 5B, it can be observed that the simulation, performed using program-generated reduced mixtures, yields organic phases substantially similar to the experimental atomic distribution of the organic phase. RMSE values for experimental and simulated atomic fractions in the organic phases were 5.88%, 0.82%, 3.99%, and 8.78% for C, H, N, and O, respectively. The result of one-way ANOVA performed together with the Tukey's test has shown that differences between simulated and experimental values for all of the atomic fractions were insignificant (p=0.061>α; p=0.999>α; p=0.974>α; α=0.05 for C, H, and N, respectively), except for oxygen, which exhibited a slightly significant difference (p=0.014<α). Since the oxygen content was experimentally determined by the weight difference, larger deviations may be expected, taking into account that the high mineral content affects the calculation.

3.3. Comparison of Validation Parameters

The reduction method was validated on a simulation of a biofuel production process based on the pyrolysis of the macroalga *Saccharina japonica*. For that purpose, an organic phase yield (MY), a water content (WC), a higher heating value (HHV), and a chemical energy recovery (ER) were used as validation parameters. ER for both simulated and experimental organic phases was calculated using the following equation:

$$ER = \frac{\gamma_{liq.ph.} \times \frac{\gamma_{org.ph.}}{100} \times HHV_{org.ph.}}{HHV_{feed}} \quad (18)$$

where $\gamma_{liq.ph.}$ and $\gamma_{org.ph.}$ represent mass yields of the entire liquid phase and the organic phase, respectively, and $HHV_{liq.ph.}$ and $HHV_{org.ph.}$ represent higher heating values of the organic phase and the feed material, respectively.

Figure 6:
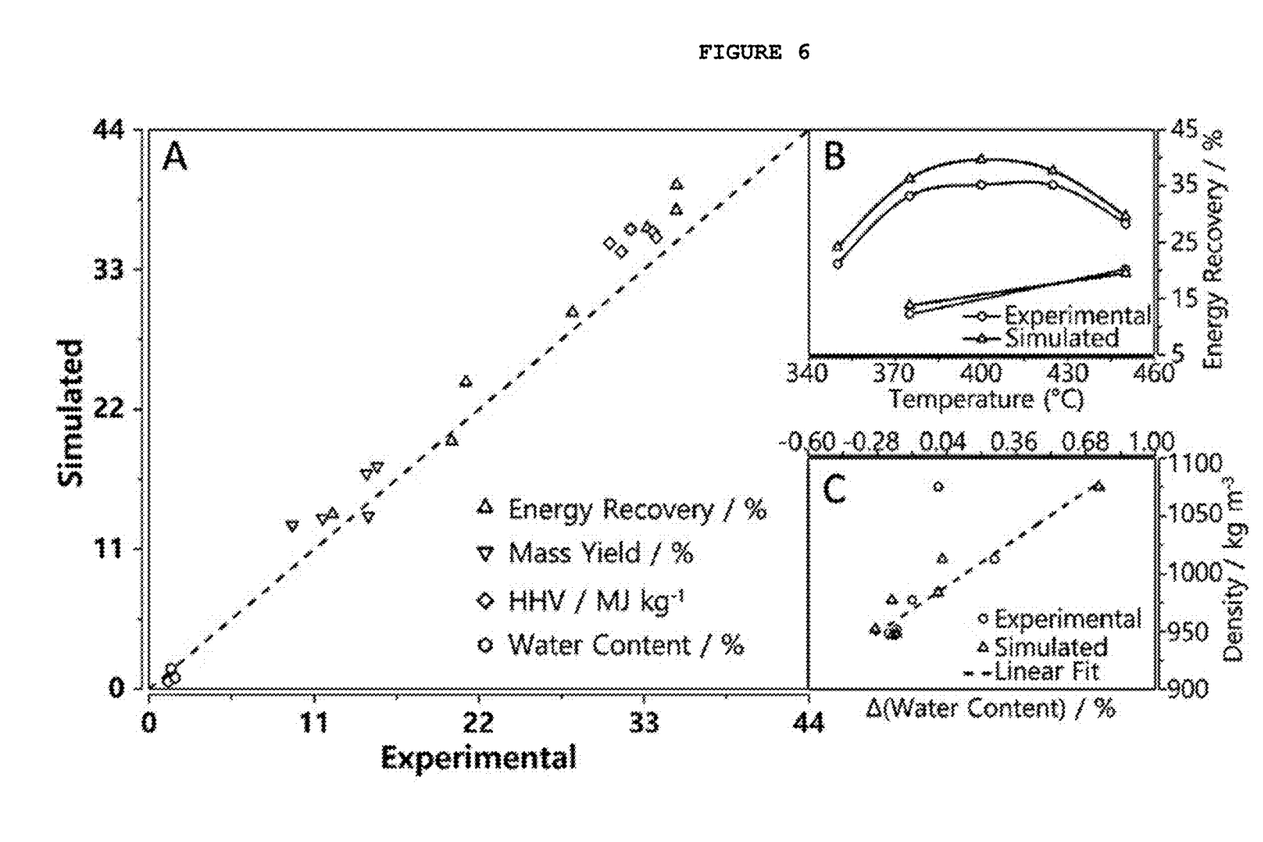
FIG. 6 shows analysis results of the dependence of experimental and simulated validation parameters (A), the dependence of experimental and simulated energy recovery on pyrolysis temperatures (B), and the dependence of a difference between experimental and simulated moisture content ($\Delta WC = WC(i) - WC(1)$) on a simulated density (C) in order to identify the effectiveness of the automated reduction method according to the present embodiment (a linear fit equation and statistical parameters: $\rho=127.14$ ($\pm 3.48$)$\times \Delta WC + 984.36$ ($\pm 3.48$), $R^2=0.95$; $p=7.57 \times 10^{-7}$; $F=99.53$).

From FIG. 6A, it can be seen that the results of the simulation using the reduced mixture closely match the experimental values having RMSE values of 2.66%, 2.32%, 3.24 MJkg$^{-1}$, and 0.65% for ER, MY, HHV, and WC. Further, none of the differences between mean values of simulated and experimental validation parameters were significant (p=0.993>α, p=0.999>α, p=0.982>α, and p=1.000>α for ER, MY, HHV, and WC, respectively). FIG. 6B shows various data points of calculated ER for experimental and simulated organic phases with respect to temperature. The arching lines represent datasets 1 to 5 (Table 1) from left to right. The two sets of data thereunder represent datasets 6 and 7. The simulated value of ER is very similar to the experimental ER trend for each of the datasets (representing different reaction conditions). Experimental and simulated water content are depicted in FIG. 6C with respect to the simulated density.

Since the simulated water content exhibits a trend almost identical to that of the experimental water content but has a slightly different bias, the difference in water content (i.e., ΔWC=WC(i)−WC(1)) is shown instead. The bias is due to the slightly higher phase separation efficiency (separation of the organic phase from the aqueous phase) in the simulation compared to experimental separation. Nonetheless, the simulation accurately reproduces a density change according to different water contents. This is evident from the result of linear regression, showing that the model is statistically significant (p=7.57×10$^{-7}$; F=99.53) (FIG. 6C).

Meanwhile, one outlying point was excluded from the linear relation due to the unreasonably high water content originating from indirect experimental data for the water content and the product of the fixed-bed reactor.

Although embodiments of the present invention have been described with reference to the accompanying drawings, those skilled in the art will appreciate that the present invention may be embodied in other specific forms without changing the technical spirit or essential features thereof. Thus, the embodiments described above should be understood to be illustrative in every way and non-limiting.

What is claimed is:

1. A method for reducing complexity of bio-crudes for process simulation, the method comprising:
   (a) obtaining experimental data of quantitative and qualitative analyses for the bio-crudes;
   (b) grouping compounds contained in the bio-crudes according to a predetermined basis based on the experimental data;
   (c) selecting representative compounds from among the compounds belonging to a same group; and
   (d) reconstituting the bio-crudes as a mixture of the representative compounds, wherein the experimental data of the quantitative and qualitative analyses are obtained using gas chromatography/mass spectrometry (GC-MS) in step (a), wherein step (b) includes:
- (b-1) classifying compounds contained in a crude oil according to the chemical group and performing grouping into upper groups;
- (b-2) classifying compounds in a same upper group according to the retention time and performing grouping into middle groups; and
- (b-3) classifying compounds in a same middle group according to the type of atoms contained in the compounds and performing grouping into subgroups, wherein in step (c), among the compounds in the same subgroup, a compound having a largest peak area on a normalized GC-MS chromatogram is selected as a representative compound of the corresponding subgroup, and wherein in step (d), peaks of compounds other than the representative compound for each subgroup are removed on the normalized GC-MS chromatogram and areas of the removed peaks are added to the peak of the representative compound.

2. A method for simulating a bio-crude process, the method comprising:
using a mixture including compounds, a number of which is reduced according to the method of claim 1, as input data.

3. A system for simulating a bio-crude process, the system comprising:
a mixture including compounds, a number of which is reduced according to the method of claim 1, as input data.

* * * * *

UNITED STATES PATENT AND TRADEMARK OFFICE
CERTIFICATE OF CORRECTION

PATENT NO. : 11,581,066 B2  
APPLICATION NO. : 16/123062  
DATED : February 14, 2023  
INVENTOR(S) : Jay Liu et al.

Page 1 of 1

It is certified that error appears in the above-identified patent and that said Letters Patent is hereby corrected as shown below:

On the Title Page

Item (73) Assignee should read:
Pukyong National University Industry-University Cooperation Foundation, Busan (KR)

Signed and Sealed this  
Seventeenth Day of September, 2024

Katherine Kelly Vidal  
*Director of the United States Patent and Trademark Office*